US010905486B2

(12) United States Patent
Faccioli (10) Patent No.: US 10,905,486 B2
(45) Date of Patent: Feb. 2, 2021

(54) DEVICE FOR EXTRACTING BONE CEMENT FROM A BONE CAVITY

(71) Applicant: Tecres S.p.A., Sommacampagna (IT)

(72) Inventor: Giovanni Faccioli, Monzambano (IT)

(73) Assignee: TECRES S.P.A., Sommacampagna (IT)

( * ) Notice: Subject to any disclaimer, the term of this patent is extended or adjusted under 35 U.S.C. 154(b) by 977 days.

(21) Appl. No.: 15/124,974

(22) PCT Filed: Nov. 27, 2014

(86) PCT No.: PCT/IB2014/066385
§ 371 (c)(1),
(2) Date: Sep. 9, 2016

(87) PCT Pub. No.: WO2015/136342
PCT Pub. Date: Sep. 17, 2015

(65) Prior Publication Data
US 2017/0020590 A1     Jan. 26, 2017

(30) Foreign Application Priority Data

Mar. 10, 2014   (IT) .............................. VR2014A0059

(51) Int. Cl.
*A61B 17/88*     (2006.01)
*A61B 17/00*     (2006.01)
*A61F 2/36*      (2006.01)

(52) U.S. Cl.
CPC ................ *A61B 17/8847* (2013.01); *A61B 2017/00477* (2013.01); *A61F 2/3662* (2013.01)

(58) Field of Classification Search
CPC ... A61B 17/8847; A61B 17/92; A61F 2/4603; A61F 2002/4619
See application file for complete search history.

(56) References Cited

U.S. PATENT DOCUMENTS 4,706,659 A * 11/1987 Matthews ............ A61B 17/164
                                                  464/173
4,919,153 A    4/1990  Chin
5,078,718 A    1/1992  Moll et al.
5,122,143 A *  6/1992  McColl ............. A61B 17/8847
                                                  606/100

(Continued)

FOREIGN PATENT DOCUMENTS

EP    0520293    12/1992
EP    1875880    1/2008
WO    00/45722   8/2000

*Primary Examiner* — Anu Ramana
(74) *Attorney, Agent, or Firm* — Tutunjian & Bitetto, P.C.

(57) ABSTRACT

Modular extractor device for removing bone cement from a bone cavity (C), including an elongated body with an axis of symmetry (X-X), a proximal end, arranged during use at the opening of the bone cavity (C), and a distal end, arranged during use at the innermost part of the bone cavity (C). The elongated body is partially hollow and is adapted to be inserted in said bone cavity (C) filled with bone cement. The elongated body includes a plurality of rigid elements coaxial to the axis (X-X) of said elongated body, partially hollow and anchored together. At least two adjacent rigid elements include a first main section, a second main section and a flange. A main section of at least one rigid element is inserted and held in position in a main section of the other rigid element of the at least two rigid elements.

17 Claims, 5 Drawing Sheets

(56) References Cited

U.S. PATENT DOCUMENTS

| | | | | |
|---|---|---|---|---|
| 5,221,282 A | * | 6/1993 | Wuchinich | A61B 17/320068 |
| | | | | 606/99 |
| 8,795,281 B2 | * | 8/2014 | Faccioli | A61B 17/8847 |
| | | | | 606/86 R |
| 9,266,178 B2 | * | 2/2016 | Eshleman | B25B 21/00 |
| 9,597,091 B2 | * | 3/2017 | Bromer | |

* cited by examiner

DEVICE FOR EXTRACTING BONE CEMENT FROM A BONE CAVITY

TECHNICAL FIELD OF THE INVENTION

The present invention relates to an extractor device for removing bone cement from a bone cavity.

STATE OF THE PRIOR ART

The technique normally used for arthroplasty provides that the application of a prosthetic device inside a bone be accompanied by the introduction, in the bone cavity where the prosthetic device will be inserted, of a certain amount of bone cement (for example, bone cement composed of acrylic resins or similar materials), which allows the prosthesis to be kept stably in position.

In the case of hip prostheses, for example, at the proximal end of the femoral bone an elongated cavity is obtained inside which the stem of the prosthesis is introduced, after interposition of a layer of fluid cement, which, once hardened, allows the prosthetic device to be fixed to the internal walls of the cavity itself.

When the need arises to remove the prosthesis for its replacement or for allowing other medical/surgical interventions in the site of implant, the same is usually removed by applying a sufficient extraction force, leaving a hollow recess inside the layer of solidified bone cement. Subsequently, it becomes necessary to eliminate the residual layer of bone cement both in the case of an implant of a new prosthesis and in the case of any further cavity interventions.

In order to eliminate such solidified bone cement layer, different types of systems intended for this purpose are known.

A first system provides for the use of ultrasound instrumentation provided with a spoon-shaped electrode.

The electrode is manually introduced by an operator inside the hollow recess and, by thermal effect induced by the ultrasounds, it allows to soften the solidified resin constituting the bone cement and, thus, withdraws it from the bone cavity by means of its spoon shape.

Such ultrasound instrumentation has some drawbacks such as the fact that it is particularly laborious and impractical to use for the operator, who is forced to handle the spoon-shaped electrode in a particularly narrow space, such as a cavity formed in a femoral bone.

In order to carry out such operation, moreover, it is necessary to have highly specialized medical staff having sufficient experience and expertise.

Moreover, the use of a heating electrode in proximity to the internal walls of the bone involves the risk of excessively increasing the temperature of the bone itself, with the risk, as known, of compromising the toughness and health status thereof.

To limit this drawback, these ultrasound instrumentations are usually provided with a sounding device which alerts the operator of the approaching to the bone walls; the efficiency of such devices, however, is usually rather limited and does not make the use of ultrasounds free from risks.

Another drawback of this technique is that it is particularly costly in terms of energy and its overall cost is not negligible.

A different technique for the extraction of cement from bone cavities is described in U.S. Pat. No. 4,919,153 and consists of injecting a fluid mass of fresh cement into the bone cavity directly in contact with the solidified cement layer left after the extraction of the prosthesis, immersing a shaped shaft with irregular outer surface in the fluid mass, allowing the fluid mass to harden and adhere to the shaft and, finally, applying an extraction force to such shaft so as to remove it from the bone cavity together with the cement.

Also this technique, however, is not free from drawbacks, such as for example the fact that it requires the application of a very large extraction force to remove, with a single operation, all of the cement hardened inside the cavity, with the risk of excessive stressing the bone of the individual who undergoes the intervention.

To overcome this drawback, a system similar to the previous one is known from U.S. Pat. No. 5,078,718, with the difference that the object which is inserted into the fluid mass of cement consists of an elongated sleeve, internally hollow, inside which a shaft is inserted for extracting the sleeve itself and the bone cement solidified inside the cavity. Such sleeve is made of different longitudinal portions aligned with each other, which comprise means for the connection to the shaft arranged inside the sleeve.

Once the fluid mass of cement has hardened and the sleeve is made integral thereto, the shaft or internal screw is removed in order to selectively extract the various longitudinal portions of the sleeve, starting from that closest to the proximal end of the femoral bone, thereby removing successive levels of cement.

Such technique, while, on the one hand, allowing to overcome the drawbacks of the prior art described above, on the other hand, it is not easy and practical to implement and is susceptible of further improvements. Moreover, the cement is likely to penetrate between a portion and the other of the sleeve, compromising the functionality thereof. From EP 0 520 293, instead, an analogous system for extracting cement is known, consisting of a threaded shaft to which some nuts are threaded in longitudinally spaced positions.

The threaded shaft is immersed in fresh cement together with the nuts and, after solidification of the cement, it is extracted by rotating it about its own axis while the nuts remain embedded in the hardened cement at different depths.

Thereafter, by means of suitable extraction screws the nuts are extracted one by one, driving therewith the different longitudinal portions of cement.

Also this extraction system has several drawbacks, such as for example the fact that it requires long and laborious manual operations for preparing the threaded shaft, onto which all the nuts necessary for completing the intervention are to be engaged one by one.

Moreover, very serious complications and problems can arise with such system in case of difficulties in the extraction of the threaded shaft from the hardened cement.

In fact, in case the threaded shaft remains blocked in the cement, the space inside the bone cavity is completely occupied by the hardened cement and the threaded shaft, not leaving any room for gradually removing the cement from the outside; in such circumstances, it is therefore necessary to resort to the physical opening of the femoral bone, with dire consequences for the patient.

It is also pointed out that, in the implementation of the above mentioned methods described in U.S. Pat. Nos. 4,919,153, 5,078,718 and EP 0 520 293, there are numerous cases in which at the end of the extraction, a more or less extended amount of hardened bone cement, conventionally called "distal plug", remains at the bottom of the bone cavity.

The removal of the distal plug is performed by means of successive additional operations that consist of drilling the plug and obtaining a hole therein, inserting a self-tapping screw into the hole thus formed and, finally, extracting the self-tapping screw together with the plug.

These additional operations can be particularly inconvenient and impractical, especially in the step of drilling the distal plug.

In order to be able to drill the distal plug properly and without dangers for the patient, in fact, it is necessary to use an anti-buckling centering bushing, an operation that is neither easy nor simple.

From EP 1 875 880 in the name of the same Applicant an equipment is known adapted to remove the bone cement from a bone cavity, comprising an elongated body, internally hollow, adapted to be inserted inside a bone cavity filled with cement, and an extraction shaft thereof, that can be inserted into the hollow body. The hollow body comprises a plurality of rigid elements, aligned with one another and means for the connection with the extraction shaft.

The rigid elements are associated with one another by means of the interposition of spacer elements of substantially tubular shape and coaxial with the elongated body; the spacer elements and the rigid elements are associated by means of the interposition of temporary couplings of the interlocking type.

A drawback of such equipment is that it is a complex device, composed of a plurality of different elements variously coupled together.

Therefore, the main task of the present invention is to provide a device for removing bone cement from a bone cavity that allows the aforesaid drawbacks of the prior art to be overcome, by developing a simple, rational and low cost solution.

Another object of the present invention is to provide for the extraction of cement from a bone cavity in a practical, easy and very efficient manner for the operator who carries out the intervention and in conditions of maximum safety and tranquility for the individual who undergoes the operation.

SUMMARY OF THE INVENTION

An object of the present invention is to improve the state of the art.

Another object of the present invention is to develop an extractor device for removing bone cement present in a bone cavity in a safe and effective.

A further object of the present invention is to develop an extractor device for removing bone cement from a bone cavity which is simple and fast to obtain.

Another object of the present invention is to develop an extractor device for removing bone cement from a bone cavity that has a low cost.

In accordance with an aspect of the invention an extractor device for removing bone cement according to one aspect of the present invention is provided.

The present specification refers to preferred and advantageous embodiments of the invention.

BRIEF DESCRIPTION OF THE DRAWINGS

Further characteristics and advantages of the invention will be clearer from the description of an extractor device for removing bone cement, illustrated by way of indication in the enclosed set of drawings wherein.

DETAILED DESCRIPTION OF THE INVENTION

With reference to the enclosed figures, a modular extractor device 1 for removing bone cement from a bone cavity is illustrated.

With particular reference to FIGS. 6-9, O generally indicates a femoral bone at whose proximal end a bone cavity C is formed.

The stem of a hip prosthesis P is inserted in the bone cavity C by the interposition of a cement layer S in a per se known manner.

Once the prosthesis P has been removed, the bone cavity C is covered by the hardened cement layer S and may, preferably, be filled with fresh cement F.

Fresh cement F has the ability to partially dissolve and soften the layer of cement S and, if allowed to harden, to form a single body S+F with the cement layer S.

The formed mass of hardened cement S+F can be removed by means of the extractor device 1 according to the present invention.

Figure 1:
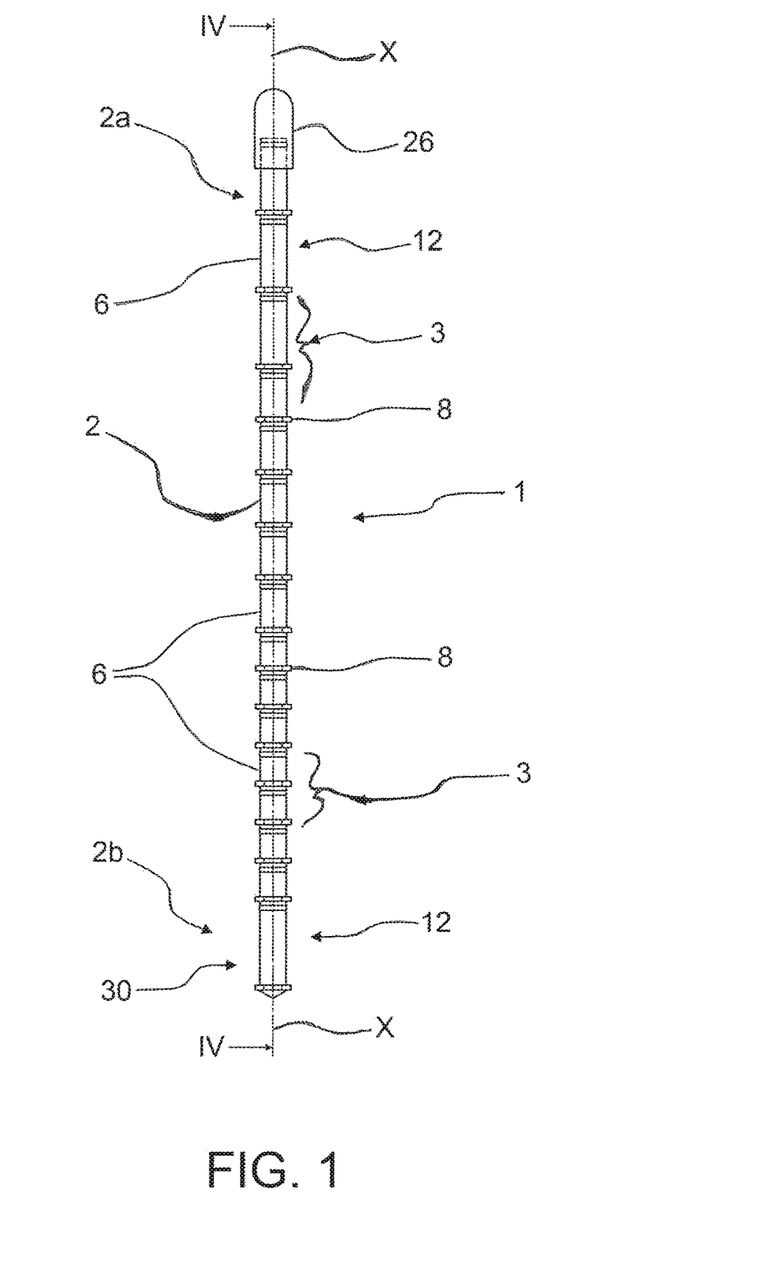
FIG. 1 is a side view of an extractor device for removing bone cement according to the present invention.

The extractor device 1, in particular, comprises overall, an elongated body 2. The elongated body 2 is at least partially internally hollow andelongated body 2 has a preferably circular cross section, taken along a plane perpendicular to the symmetry or longitudinal axis X-X thereof.

The elongated body 2 has axis of central or longitudinal symmetry X-X and a proximal end 2a, intended to be arranged, during use, at the opening of the bone cavity C and a distal end 2b, intended to be arranged, during use, at the innermost part of the bone cavity C.

The extractor device 1 or the elongated body 2 thereof can be inserted into the bone cavity C, in order to be immersed in fresh cement F.

The elongated body 2 comprises a plurality of mutually aligned rigid elements 3 and, in this respect, the elongated body 2 or the extractor device can be defined as modular.

The various rigid elements 3 constitute the elongated body 2 of the extractor device 1; in particular, the elongated body 2 comprises at least two rigid elements 3.

The various rigid elements 3 are, preferably, coaxial to the elongated body 2 and coaxial to each other, that is, they are substantially arranged along the same axis X-X.

Preferably, the rigid elements 3 have substantially the same configuration but different dimensions, as will be better described in the following of the present description.

The rigid elements 3 have at least partially, a substantially tubular configuration, having a substantially circular cross section. Preferably, at least part of the lateral external and/or internal wall of the rigid elements 3 is substantially tubular with circular cross section.

In an alternative version of the invention, at least part of the external and/or internal lateral wall of the rigid elements has a cross section which may not be circular but rather substantially regular or irregular polygonal.

Each rigid element 3 has a proximal end 4, intended to be facing, during use, towards the opening of the bone cavity C, as well as a distal end 5, opposite the proximal end 4 and intended to be facing, during use, towards the deepest portion of the bone cavity C.

Each rigid element 3 is at least partially hollow.

More in detail, the rigid element 3 comprises a first main section 6 having a diameter or external width or lateral bulk d', a second main section 7 having a diameter or external width or lateral bulk d", and at least one flange 8, preferably intermediate, having diameter or external width or lateral bulk D.

The first main section 6 and the second main section 7 have a substantially cylindrical or annular configuration having a substantially circular cross section.

In an alternative version of the invention, the first main section 6 and the second main section 7 have a substantially prismatic configuration having a substantially polygonal cross section.

In yet another alternative version, at least one from among the first main section 6 and the second main section 7 has a substantially cylindrical configuration having a substantially circular cross section.

The first main section 6 and the second main section 7 extend, preferably, one from a side opposite to the other with respect to the flange 8 which in this case is intermediate therebetween.

In an alternative version that will be better illustrated hereinafter, the flange 8 is arranged at the distal end 5 of the rigid element 3.

The flange 8 has a substantially disc-shaped or annular or prismatic configuration, coaxial to the axis X-X of the elongated body 2 and has a substantially circular or polygonal external cross section.

Alternatively, it can be provided that the flange 8 is composed of a series of curved sections or angular sectors extending at a same level of a same main section and are mutually angularly spaced with respect to the axis X-X.

When the flange 8 has a prismatic configuration, the external cross section thereof is preferably hexagonal or octagonal.

The prismatic configuration of the flange 8, being provided with at least one corner, enables the creation of weakening points and consequent fracture lines in the bone cement S+F, so as to facilitate and make more precise the extraction of a mass of cement S'+F', according to the method indicated further below.

The flange 8 projects externally and transversely with respect to the axis X of the elongated body 2; that is to say, the flange 8 is adapted to protrude towards the lateral walls of the bone cavity C, with respect to the first and the second main section 6, 7. The external diameter or width or external lateral bulk D of the external wall of the flange 8 is greater than the external diameter or width or external lateral bulk of the first 6 and/or second main section 7. In other words, the flange 8 is wider than such first 6 and second 7 sections.

The first main section 6, in a version of the invention, has a diameter or lateral bulk d' that is greater than the diameter or lateral extension d" of the second main section 7. Moreover, the first main section 6 and/or the rigid element 3 have an axial longitudinal port or opening 9.

The port or opening 9 is coaxial to the axis X-X of the elongated body 2 of the extractor device 1, that is to say, it has substantially the same axis as the elongated body 2.

The port or opening 9 extends longitudinally for at least part of the first main section 6 or extends for the whole longitudinal extension of the first main section 6, or extends for at least part of the rigid element 3.

In particular, the port or opening 9 has a configuration substantially corresponding to that of the second main section 7, provided that the second main section 7, during use, is arranged inside such port or opening 9 of another subsequent or adjacent rigid element 3.

In this regard, the overall dimensions of the port or opening 9, delimited by the first main section 6, are slightly greater than or substantially equal to those of the second main section 7, so that the second main section 7 of a rigid element 3 is housed to size in the port or opening 9 of the first main section 6 of another or subsequent rigid element 3.

The port or opening 9 has a diameter d''' or a lateral bulk or a dimension that is slightly greater than or substantially equal to the diameter or lateral extension d" of the second main section 7.

At the same time, the size of the port or opening 9 can allow a limited play or mobility of the second longitudinal section 7 inside the port or opening 9, so that it is possible to lightly bend and manually shape the elongated body 2 in order to better adapt the elongated body 2 to the configuration of the bone cavity C, both along a straight axis and along a curved axis of the same.

Figure 5:
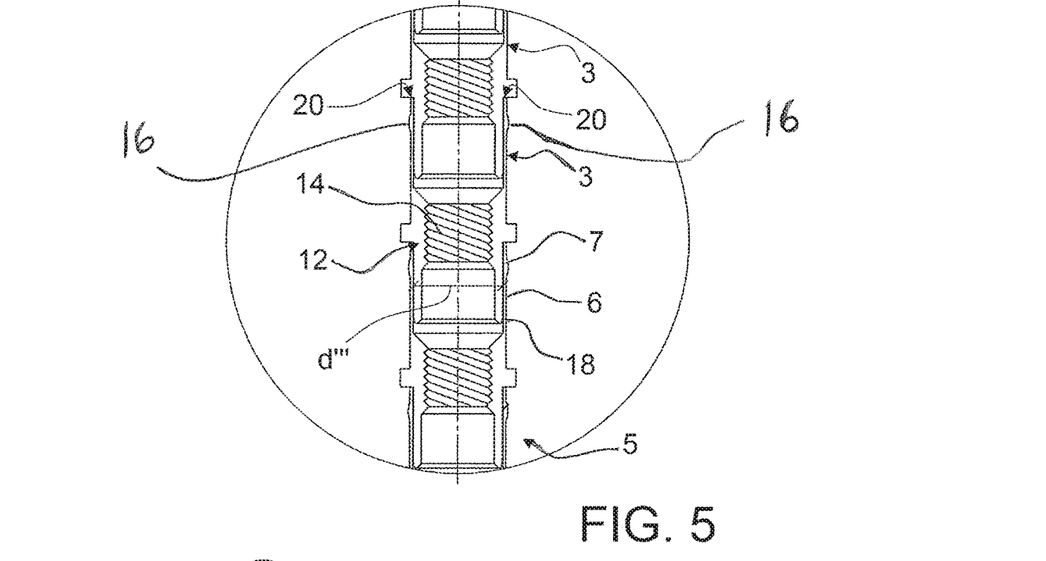
FIG. 5 is an enlarged detail of FIG. 4.
Figure 6:
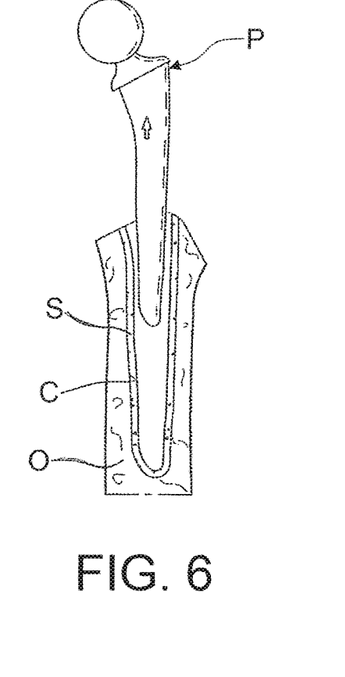
FIGS. 6 to 9 illustrate several steps of bone cement extraction by means of the extractor device of the previous figures.
Figure 7:
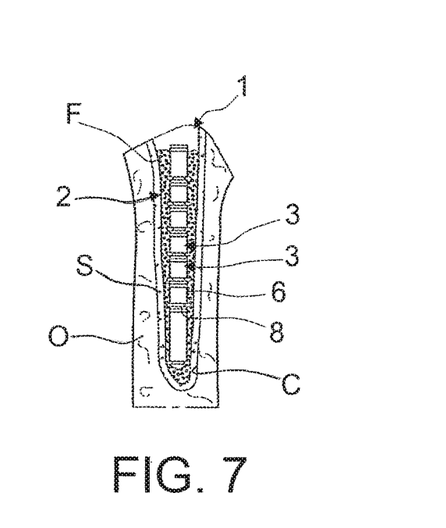
Figure 8:
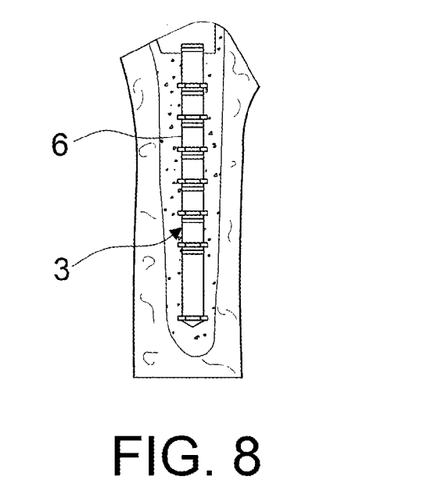
Figure 9:
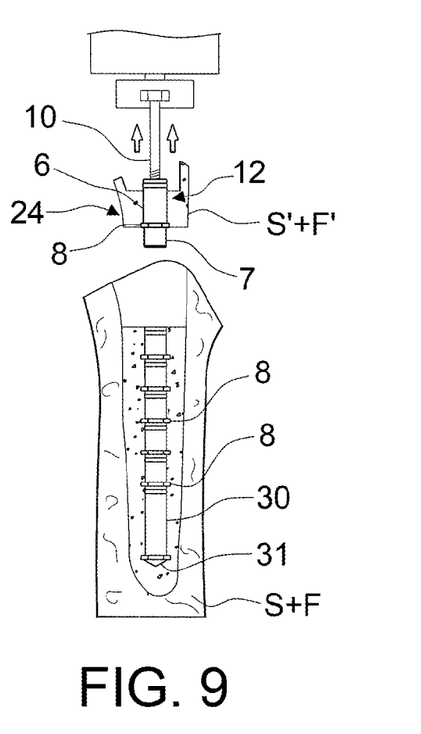

As it can be appreciated from FIG. 5, the first main section 6 has a tubular configuration and has a lateral wall having a thickness as low as few tenths of a millimeter. In this way, at least some elasticity can be imparted to the material constituting the first main section 6, so it can be adapted to determine interference fit and interlocking, preferably to size, with the second main section 7 of an adjacent and subsequent or preceding rigid element that is housed within the first main section 6.

In this regard, the free end of the second main section 7 that is insertable in the port or opening 9, could comprise an inlet section 18 having a section that decreases towards an outside or a free edge, so as to allow an easier insertion of the second main section 7 and a simultaneous widening in the port or opening 9 of an adjacent or subsequent rigid element 3. This arrangement in particular, would allow the second main section 7 and the port or opening 9 to be realized substantially of the same size.

In particular, the external cross section of the port or opening 9 of such first main section 6, in a version of the invention, is slightly different with respect to that of the second main section 7, so as to precisely facilitate such interlocking between the components of adjacent rigid elements.

Such interference fit is made more stable and safer by the presence of an annular enlargement 16, arranged in the external wall of the first main section 6, at the upper edge thereof, and arranged at the proximal end 4 thereof. Such annular enlargement is extended transversally and externally with respect to the axis X-X of the elongated body 2.

In particular, the outer projection of such annular enlargement 16 is greater than the external diameter or lateral bulk d' of the first main section 6.

In particular, the insertion of the second main section 7 of a rigid element 3 in the port or opening 9 of the first main section 6 of another or subsequent or adjacent rigid element 3, provides that the flange 8, preferably intermediate, of the first rigid element 3 abuts against a preferably upper edge 20 arranged at the proximal end 4, of the other or subsequent or adjacent rigid element 3.

The abutment between the flange 8 of a first rigid element 3 and the edge 20 of the subsequent or adjacent rigid element 3 can also occur in a distal position 5 of such first rigid element 3, as will be described according to a further version of the present extractor device 1.

In this way, the port or opening 9 of the other or subsequent or adjacent rigid element 3 is preferably sealingly closed and substantially completely covered by the flange 8 of the first rigid element 3, preventing the entrance therein of fresh cement F inserted in the bone cavity C in order to extract the mass of solidified cement S+F.

Therefore, the rigid elements 3 are coupled to each other by means of temporary coupling of the interlocking type, allowing the joining of the various rigid elements 3 until an axial separation force of predetermined magnitude is applied therebetween. The extractor device 1 further comprises an end element 30 arranged at the distal end 2b of the elongated body 2.

The end device 30 also has a first main section 6 delimiting a port or opening 9 adapted to house (substantially to size) the second main section 7 of the rigid element 3.

However, instead of the second main section 7, the end element 30 has a tip section 31, having a substantially conical or pyramid-shaped closed configuration.

The terminal section 30 can comprise a flange 8, preferably intermediate, similar to that already described for the rigid element 3.

The rigid elements 3, and in particular, at least each of their first main sections 6, can have different dimensions from each other.

Figure 2:
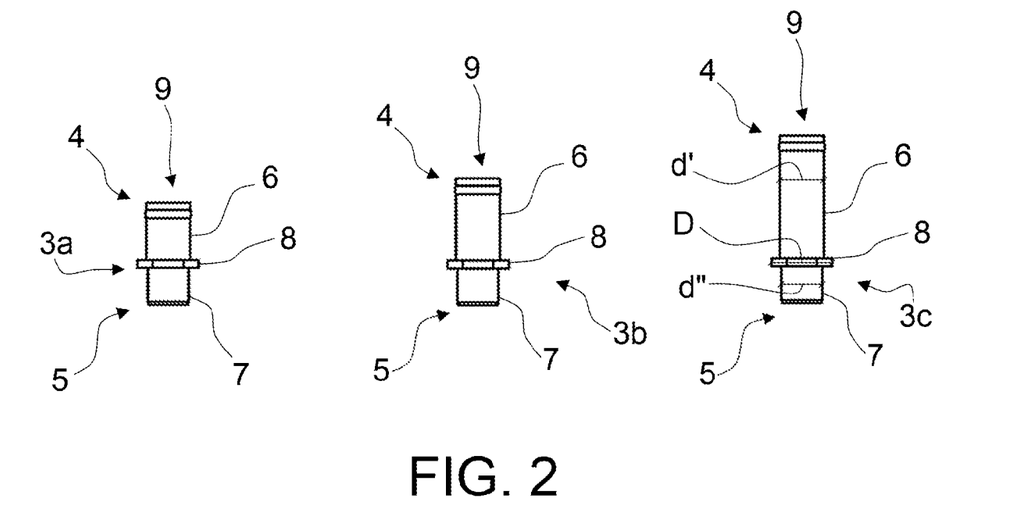
FIG. 2 is a side view of a component of the extractor device for removing bone cement of FIG. 1.
Figure 3:
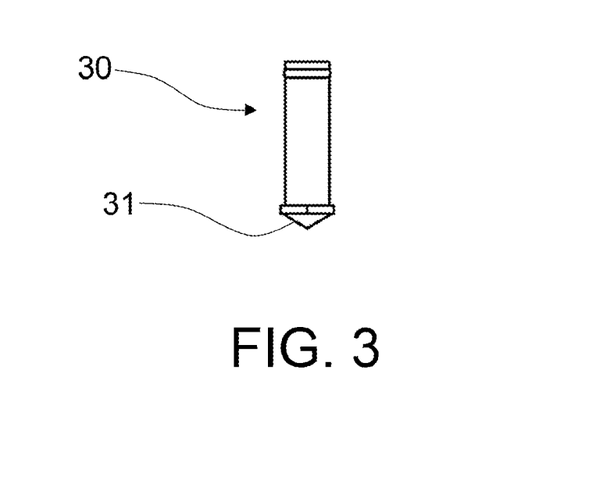
FIG. 3 is a side view of a further component of the extractor device for removing cement of FIG. 1.
Figure 4:
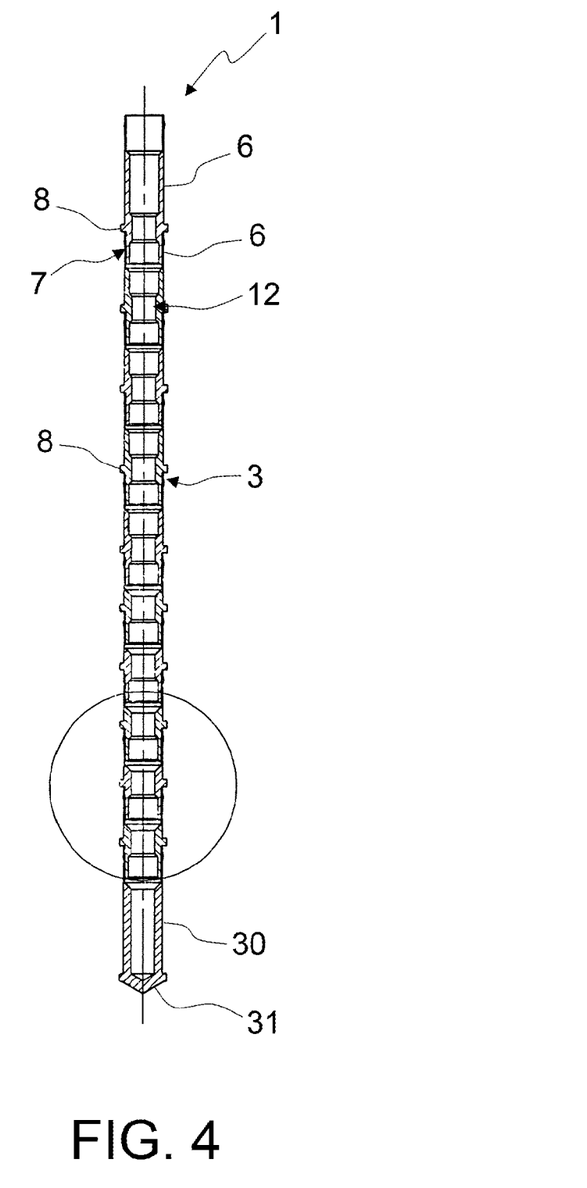
FIG. 4 is a sectional view taken along the plane of trace IV-IV of the extractor device of FIG. 1.

That is to say, the longitudinal extension (considered along a direction parallel to that of the axis X-X of the elongated body 2) of the first main section 6 can have different lengths. For example, the length of the first main section 6 of the rigid element 3a is lower than the length of the first main section 6 of the rigid element 3b, which in turn is lower than the length of the first main section 6 of the rigid element 3c, as shown in FIG. 2.

Advantageously, considering the configuration of the bone cavity C and of the extraction forces required, the elongated body 2 can have at least one rigid element 3c at the proximal end 2a, at least one rigid element 3b in its central portion and a least one rigid element 3a at the distal end 2b.

Naturally, depending on the specific needs, the overall length of the elongated body 2 may vary and the arrangement of the rigid elements 3a, 3b, and 3c may be varied accordingly.

Moreover, the arrangement of the rigid elements 3a, 3b, 3c can be selected as desired, depending on the specific needs of the patient; it is also possible that an extractor device comprises only one type of rigid elements 3a or 3b or 3c.

The configuration of the rigid elements 3, 3a, 3b, 3c ensures that the second main section 7 of a rigid element 3, 3a, 3b, 3c can be sized to be housed in the port or opening 9 present in another or subsequent or adjacent rigid element 3, 3a, 3b, 3c, irrespective of their length or extension, or can be housed in the port or opening 9 present in the end section 30.

Each rigid element 3 comprises the first main section 6, the flange 8 and the second main section 7 stably fixed to one another and, preferably, all made in a single piece.

Also the end element 30 comprises the first main section 6, the tip section 31 and the optional flange 8 stably fixed to one another and, preferably, all made in a single piece.

In this way, the elongated body 2 is made of a smaller number of components with respect to the state of the art, greatly simplifying its implementation and the associated costs.

Likewise, the assembly and use of the elongated body 2 of the extractor device 1 is also simpler and easier, even in the presence of not particularly experienced operators.

The various rigid elements 3 and the end element 30 are advantageously made of a biocompatible metal, such as for example stainless steel.

Naturally, the first main section 6 and the second main section 7 can be reversed, the latter having a more proximal position with respect to the other, without departing from the scope of protection of the present invention.

Figure 10:
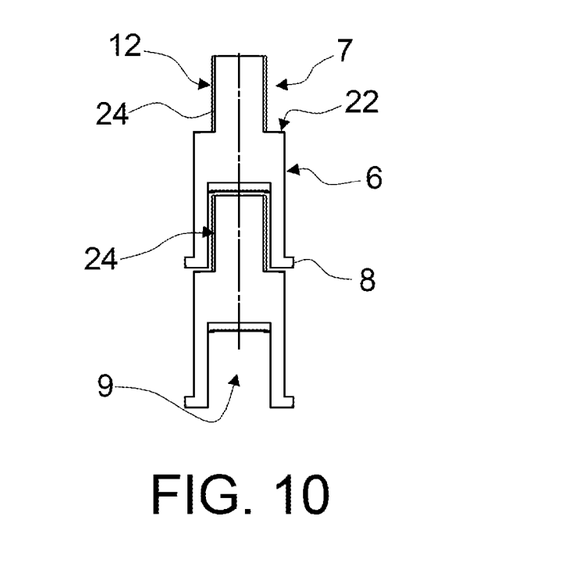
FIG. 10 is a side view of an embodiment of the extractor device according to the present invention.

This is for example, illustrated in FIG. 10.

A further version of the present invention is illustrated in FIG. 10. In such a version, the second main section 7 has a free end, preferably at the proximal end 4 of the rigid element, and another or second end in contact with the first main section 6, and the latter has a free edge, positioned on the opposite side with respect to the second main section 7.

The free edge of the first main section 6 is preferably flanged or equipped with a flange 8 very similar to that previously described.

The first main section 6 delimits a port or opening 9, as indicated above, having dimensions slightly greater than or substantially equal to those of the second main section 7, so that the second main section 7 is housed to size and an interference fit is provided between the second main section 7 and the first main section 6 and/or the port or opening 9.

The rigid elements 3, therefore, are also in this case interlockingly constrained to one another, in a stable manner until the extraction of each of them is carried out due to the application of extraction forces as described below.

The first main section 6, due to the fact that it delimits the port or opening 9 having slightly larger or substantially equal dimensions to those of second main section 7, has dimensions and a diameter or lateral extension d' greater than that d" of the second main section 7.

This determines the presence, between the second main section 7 and the first main section 6, of a shoulder or abutment surface 22 (similar to the edge 20 previously described).

The flanged free edge or flange 8 of a subsequent or adjacent rigid element 3 is in abutment against such abutment surface 22.

The extractor device 1 is further provided, in a version of the invention, with an extraction shaft 10 of the elongated body 2, once the elongated body 2, embedded in fresh cement F, has become integral with the mass of hardened cement S+F.

The extraction shaft 10 can be inserted along at least part of the elongated body 2 and/or along the port or opening 9 of the rigid elements 3 or of the end element 30, and can be associated to the latter.

In fact, for this purpose, the rigid elements 3 and the end element 30 are internally provided with means 12 for removable engagement with the extraction shaft.

Such engagement means 12 are therefore adapted to connect and removably engage each rigid element 3 and/or the end element 30 with the extraction shaft 10.

Such engagement means 12 can be of the threaded type or engagement means of the bayonet type or other removable engagement means intended for this purpose.

In a version in which such engagement means 12 are of the threaded type, the rigid elements 3 comprise a mother screw 14. Such mother screw 14 is formed on the inner surface of each rigid element 3, at the distal end 5 thereof. In particular, such mother screw 14 is formed on the inner surface of the port or opening 9 of the first main section or, (in case such port or opening 9 is axially extended at the area of the flange 8) the mother screw 14 is obtained at such area, or, (advantageously, in case such port or opening 9 is axially extended at at least part of the second main section 7) such mother screw 14 is obtained at such at least part of the second main section 7. The presence of the mother screw 14 at the area of the flange 8 imparts greater solidity to the engagement and connection with the extraction shaft 10, so that a greater toughness is obtained between the various engaged components, so as to withstand the high traction forces to be applied in order to extract the mass of cement S'+F'.

The mother screw 14 present inside the rigid element 3 is adapted to be engaged by screw means or by an external threading 24 formed at the distal end of the extraction shaft 10. In detail, the external threading 24 is extended on the extraction shaft 10 for a length substantially lower than the distance defined between two mother screws of two consecutive rigid elements 3, so that it cannot engage two or more rigid elements 3 at the same time.

Moreover, in such version, also the end element 30 has a mother screw 14 in its internal wall, adapted to be removably connected with the extraction shaft 10. Also, in this case, in order to distribute the extraction forces as efficiently as possible, the mother screw 14 (or in general the engagement means 12) is positioned in the most distal part of the rigid element 3 or of the end element 30.

Alternatively, if the rigid elements 3 have an external threading 24 on the external lateral wall of the second main section 7 (not affected by the bone cement since the second main section 7 is housed in the port or opening 9 of the first main section 6), the distal end of the extraction shaft 10 comprises a corresponding mother screw.

In a version in which the engagement means 12 are of the bayonet type, they are adapted to removably engage the internal wall of each rigid element 3 with the distal end of the extraction shaft 10.

The exemplary operation of at least one version of the present invention is as follows.

During the step preceding the intervention on the patient, the operator can manually shape the elongated body 2 depending on the type of bone cavity C in which it is to be inserted, shaping it along a rectilinear or curvilinear axis or a combination of both. Once the hip prosthesis P has been extracted, the recess left by the stem of the prosthesis is filled with the fresh cement F.

At this point, the elongated body 2 is immersed in fresh cement F and is left in this position until complete hardening occurs of the fresh cement F, which stably adheres to the layer of hardened cement S, determining the formation of a cement mantle S+F. Moreover, the elongated body 2 is stably incorporated in the cement mantle S+F, becoming an integral part of the latter.

Thereafter, the insertion of the extraction shaft 10 into the elongated body 2 is carried out, as well as the removable engagement of the engagement means 12 (present in each rigid element 3) and, thereafter, in the end element 30 with respective complementary removable engagement means present in the distal end of the extraction shaft 10. In a version in which such engagement means 12 are of the threaded type, such step can occur, for example, by means of screwing of the external threading of the extraction shaft 10 into the mother screw 14 of the first rigid element 3 (arranged at the proximal end 2*a* of the elongated body 2).

By means of a hammer device of per-se know type, an impact force of traction type is applied to the extraction shaft 10 which, by means of the rigid element 3 arranged at the proximal end 2*a* of the elongated body 2, is transmitted to the portion S'+F' of the mass of hardened cement S+F arranged therearound.

As a consequence of such impact force, the portion S'+F' of cement is separated from the rest of the mass of hardened cement S+F and, thus, extracted from the bone cavity C.

By repeating the operation for each of the rigid elements 3 and for the end element 30 embedded in cement, the mass of hardened cement S+F can be removed completely or almost completely.

It is noted that, once the end element 30 arranged at distal end 2*b* of the elongated body 2 has been extracted, it is possible that a distal plug of hardened cement remains at the bottom of the bone cavity C; such plug is able to be removed by means of conventional drilling and extraction techniques by means of a self-tapping screw.

In this case, the particular shape of the end element 30 arranged at the distal end 2*b* of the elongated body 2 and of the conical or pyramid-shaped surface of the tip section 31 thereof, allows impressing, on the distal plug, a hollow shape acting as a inlet and centering for the tip of the drill, allowing to facilitate and significantly simplify the plug removal operation.

Moreover, the fact that each rigid element 3 and that the end element 30 are respectively composed of several parts in a single piece, ensures that the extraction of the cement occurs in an effective and efficient manner, eliminating the risk that, with the mass of cement S'+F', only the component or components directly constrained or overlying the engagement means and engaging the extraction shaft are extracted, which would thereby compromising the subsequent operation of the extractor device.

Moreover, the fact that the extractor device is made of metal and not of plastic materials (that may possibly undergo "softening" due to the fresh cement resulting in loss of their mechanical properties), provides an advantage in terms of safety, as compared to other solutions available in the prior art.

Moreover, due to the fact that the flange 8 projects externally with respect to the main sections 6, 7, a sort of recessed area is created between one flange and the next flange in which fresh cement can be inserted, further facilitating the extractor device being integral with the hardened cement S+F. This enables the extraction of the mass S'+F' to be performed effectively by means of the present invention. The various flanges 8 of the elongated body 2 further create a sort of step in the cement, even more so when the same have a substantially prismatic configuration, thus acting as an inlet for the fracture lines that will be generated in the cement itself after application of the extraction forces provided, further ensuring the correctness of the extraction required.

The extractor device 1 can comprise a cap 26, for example, made of silicone or plastic material, which is fit on the most proximal rigid element 3, for example, during the steps of transport or insertion of the extractor device in the bone cavity C.

Such cap 26 acts as a protection of such rigid element 3 and prevents its port or opening 9 from being inadvertently moved or clogged.

It has been therefore observed how the described invention achieves the intended objects.

The various characteristics described for a version of the invention may also be present in the other versions described, without departing from the indicated scope of protection.

The present invention thus conceived is susceptible to numerous modifications and variants all falling within the scope of protection offered by the claims.

The invention claimed is:

1. A modular extractor device for removing bone cement from a bone cavity, comprising:
   an elongated body that has a longitudinal axis, a proximal end, arranged, during use, at the opening of the bone cavity, and a distal end, arranged, during use, at the innermost part of the bone cavity,
   wherein said elongated body is at least partially internally hollow and is suitable for being inserted in said bone cavity filled with bone cement,
   wherein said elongated body comprises a plurality of rigid elements coaxial to the longitudinal axis of said elongated body, wherein said plurality of rigid elements are at least partially hollow,
   wherein at least two adjacent rigid elements of said plurality of rigid elements each comprise a first main section, a second main section and a flange, wherein at least said first main section defines an axial opening, wherein a free end of the second main section of at least one rigid element of said at least two adjacent rigid elements is inserted into and held in position inside the axial opening of the first main section of the other rigid element of said at least two adjacent rigid elements, to facilitate interlocking between the at least two adjacent rigid elements,
   wherein at least one of said first main section and said second main section has a substantially cylindrical configuration having a substantially circular external cross section or a substantially prismatic configuration having a substantially polygonal external cross section, wherein each of said external cross sections of said first main section and said second main section has a diameter,
   wherein said flange has a substantially disc-shaped or annular or prismatic configuration, the flange having a diameter or width that is greater than the diameter of said first main section and/or of said second main section, and
   wherein said flange protrudes outwards from a circumferential outer surface of the main section, transverse to the longitudinal axis of the elongated body to form a protrusion that is continuous around the circumference of the elongated body.

2. The extractor device according to claim 1, wherein said flange has at least one of a substantially disc-shaped or prismatic configuration.

3. The extractor device according to claim 1, wherein said elongated body comprises an end element arranged at the distal end of said elongated body, said end element comprising at least one of a first main section delimiting an opening, a flange and a tip section, wherein said tip section has a substantially conical or pyramid shape.

4. The extractor device according to claim 3, wherein at least one of said end element and at least said first main section of said end element has an axial opening having a diameter that is greater than or substantially equal to the external diameter of the second main section of a rigid element that is adjacent to said end element, so that it is possible to insert said second main section of a rigid element in said axial opening of said end element.

5. The extractor device according to claim 3, wherein said flange of said first rigid element is intermediate between said first main section and said second main section of said first rigid element and is in abutment against an edge of said first main section of an adjacent rigid element or of said end element.

6. The extractor device according to claim 3, wherein said extractor device comprises an extraction shaft, wherein said extraction shaft is able to be inserted along at least part of said elongated body and/or along said axial opening of said rigid elements or of the opening of said end element.

7. The extractor device according to claim 6, wherein said rigid element and/or said end element comprise removable engagement means for removably engaging said extraction shaft.

8. The extractor device according to claim 7, wherein said removable engagement means are threaded or a bayonet.

9. The extractor device according to claim 8, wherein said removable engagement means comprise an external threading formed on the outer surface of said second main section, and external threading arranged at a distal end of said extraction shaft.

10. The extractor device according to claim 7, wherein said removable engagement means comprise a threading formed on the inner surface defining said axial opening, and complementary external threading arranged at a distal end of said extraction shaft.

11. The extractor device according to claim 3, wherein at least one of said rigid elements and said end element are made from a biocompatible metal.

12. The extractor device according to claim 1, wherein said axial opening has a diameter that is greater than or substantially equal to the external diameter of the second main section of a second rigid element that is at least one of adjacent and subsequent or adjacent and preceding to said first rigid element, so that it is possible to insert said second main section of said second rigid element in said axial opening of said first rigid element.

13. The extractor device according to claim 1, wherein said second main section has an end in contact with said first main section and wherein said first main section has an edge, positioned on the opposite side with respect to said second main section, wherein said edge of said first main section is equipped with the flange.

14. The extractor device according to claim 13, wherein between said second main section and said first main section further comprising an abutment surface, wherein said flange of said first main section of said first rigid element is in abutment against said abutment surface of said adjacent rigid element.

15. The extractor device according to claim 1, wherein said first main section has an annular enlargement projecting transversally and externally with respect to the longitudinal axis of the elongated body, wherein said annular enlargement is arranged on an outer surface of said rigid element.

16. The extractor device according to claim 1, wherein a longitudinal extension of the first main section of one of said plurality of said rigid elements has a length different from the length of the longitudinal extension of another one of the plurality of said rigid elements.

17. A modular extractor device for removing bone cement from a bone cavity, comprising:
   an elongated body that has a longitudinal axis, a proximal end arranged at the opening of the bone cavity, and a distal end arranged at the innermost part of the bone cavity, wherein said elongated body is at least partially internally hollow;
   wherein said elongated body comprises a plurality of rigid elements aligned with one another and coaxial to the longitudinal axis of said elongated body, wherein said plurality of rigid elements are at least partially hollow, wherein adjacent rigid elements of said plurality of rigid elements each comprise a first main section, a second main section and a flange, wherein at least said first main section defines an axial opening, wherein a free end of the second main section of at least one rigid element of said adjacent rigid elements is inserted into and held in position inside the axial opening of the first main section of the other rigid element of said adjacent rigid elements, to facilitate interlocking between the adjacent rigid elements, wherein each external cross section of said first main section and said second main section has a diameter, wherein said flange has a diameter that is greater than the diameter of said at least one first main section and/or of said at least one second main section, and wherein each flange protrudes outwards from a circumferential outer surface of the main section, transverse to the longitudinal axis of the elongated body to form a protrusion that is continuous around its circumference, and wherein the protruding circumferentially continuous flanges are provided along an entire length of the device.

* * * * *